(12) United States Patent
Critser et al.

(10) Patent No.: US 6,218,101 B1
(45) Date of Patent: Apr. 17, 2001

(54) ENZYMATIC METHOD FOR REMOVAL OF CRYOPROTECTANTS FROM CRYOPRESERVED ANIMAL CELLS

(75) Inventors: John K. Critser, Carmel; Erik J. Woods, Indianapolis, both of IN (US)

(73) Assignee: General Biotechnology, LLC, Carmel, IN (US)

( * ) Notice: Subject to any disclaimer, the term of this patent is extended or adjusted under 35 U.S.C. 154(b) by 0 days.

(21) Appl. No.: 09/304,404

(22) Filed: May 4, 1999

Related U.S. Application Data

(60) Provisional application No. 60/084,158, filed on May 4, 1998.

(51) Int. Cl.$^7$ .............................. A01N 1/02; C07G 17/00; C07K 1/00
(52) U.S. Cl. ................................ 435/2; 435/267; 435/269
(58) Field of Search ............................. 435/1.1, 1.2, 1.3, 435/2, 267, 269

(56) References Cited

U.S. PATENT DOCUMENTS

| | | |
|---|---|---|
| 3,791,384 | 2/1974 | Richter et al. . |
| 3,893,308 | 7/1975 | Barkay et al. . |
| 4,007,087 | 2/1977 | Ericsson . |
| 4,429,542 | 2/1984 | Sakao et al. . |
| 4,480,682 | 11/1984 | Kaneta et al. . |
| 4,487,033 | 12/1984 | Sakao et al. . |
| 5,700,632 | 12/1997 | Critser et al. . |

OTHER PUBLICATIONS

Thorner, J. and Paulus, H., "Catalytic and Allosteric Properties of Glycerol Kinase from *Escherichia coli*," Jun. 10, 1973, *J. Biol. Chem.*, vol. 248, No. 11, pp. 3922–3932.

Sherman, J.K., "Improved Methods of Preservation of Human Spermatozoa by Freezing and Freezing–Drying," *Fertility & Sterility*, vol. 14, No. 1, pp. 49–64, 1963.

Behrman, et al., "Heterologous and Homologous Inseminations with Human Semen Frozen and Stored in a Liquid–Nitrogen Freezer," *Fertility & Sterility*, vol. 17, No. 4, pp. 457–466, 1966.

Willoughby, et al., "Osmotic Tolerance Limits and Properties of Murine Spermatozoa," *Biol. of Reproduction*, vol. 55, pp. 715–727, 1996.

Gilmore, et al., "Determination of optimal cryoprotectants for their addition and removal from human spermatozoa," *Human Reproduction*, vol. 12, No. 1, pp. 112–118, 1997.

Gilmore, et al., "Effect of Cryoprotectant Solutes on Water Permeability of Human Spermatozoa," *Biol. of Reproduction*, vol. 53, pp. 985–995, 1995.

Gao, et al., "Prevention of osmotic injury o human spermatozoa during addition and removal of glycerol," *Human Reproduction*, vol. 10, No. 5, pp. 1109–1122, 1995.

Gilmore, et al., "Osmotic properties of boar spermatozoa and their relevance to cryopreservation," *J. of Reproduction and Fertility*, vol. 107, pp. 87–95, 1996.

*Primary Examiner*—Sandra E. Saucier
(74) *Attorney, Agent, or Firm*—Barnes & Thornburg

(57) ABSTRACT

A method to remove cryoprotectants from cryopreserved biological cells and tissues is described. Enzymes are used to convert compounds used as cryoprotectants for cells during cryopreservation to membrane impermeable products. This process effectively removes the cryoprotectant chemicals from the cells prior to their use in transfusion, transplantation, insemination or other applications, without causing osmotic damage due to cell swelling. Methods are described for subsequent removal of the enzymes and enzyme conversion products from the cell and tissue preparations.

19 Claims, 1 Drawing Sheet

ENZYMATIC METHOD FOR REMOVAL OF CRYOPROTECTANTS FROM CRYOPRESERVED ANIMAL CELLS

This application claims benefit of Provisional Application No. 60/084,158 filed May 4, 1998.

FIELD OF INVENTION

The present invention relates to a method of removing chemical compounds which protect cells (cryoprotectants) during low temperature preservation (cryopreservation). More particularly, this invention is directed to the use of specific enzymes to convert cryoprotectant compounds into products which are not transported across the cell membrane. The enzymes convert cryoprotectants in solution and thereby work to shift the chemical potential of the cryoprotectant resulting in osmotic flow of cryoprotectants out of the cells and into the enzyme solution.

BACKGROUND OF INVENTION

Fresh biological cells such as sperm, red blood cells, platelets and the like, are typically viable for but a short period of time in vitro. Nevertheless, it is commercially and medically significant that such cells are available for use long after they have been collected from donors, sometimes several months or even years later. Various cryopreservation methods, have been developed to preserve biological cells for these relatively longer periods of time. For example, cryopreservation of sperm cells permits a domestic animal breeder to maintain stocks of valuable sperm cells for use when necessary; it enables the inexpensive transport of such stocks; and it ultimately permits genetically superior males to inseminate a larger number of females. Beyond livestock, artificial insemination is also used in human clinical medicine. As another example, cryopreservation of blood permits donated blood to be stored much longer that the typical 14 day storage period. Moreover, diseases carried in blood with a latency period longer than 14 days may not be discovered in the donor until the blood has been placed into a patient. Cryopreserved blood can be stored for a time sufficient to allow donors to be screened well beyond their date of donation.

The survivability of viable cells and tissues using prior art freezing methods is often quite low. Freezing conditions are relatively harsh and thermal shock or other phenomena such as ice crystal formation often destroy biological cells and tissues. Therefore, maximizing the viability of thawed cells and tissues has been the goal of many researchers.

The prior art discloses various methods for improving the survivability of frozen cells and tissues. In many cases, the cells are removed from their physiological milieu and suspended into artificial tissue culture media prior to preservation. U.S. Pat. No. 4,007,087 to Ericsson discloses a sperm fractionation and storage method which claims to increase the percentage of motile sperm that survive frozen storage. Ericsson discloses a method whereby motile sperm are separated from non-motile, defective or dead sperm. The fraction containing the motile sperm is then frozen. Ericsson reports that his method increases the fertility of a sperm sample by enhancing the environmental (the ratio of total sperm to motile sperm) and the viability (progressiveness of motility of the motile sperm) factors affecting the fertility of a sample, but his method does not improve the population (motile sperm count) factor which is possibly the most critical.

U.S. Pat. No. 3,791,384 to Richter et al. discloses a method for deep freezing and thawing boar sperm which includes inactivating the fresh sperm by means of an inactivating solution that includes dextrose, dihydrate of ethylenedinitrotetra-acetic acid, sodium hydrogencarbonate. Reicter reports that inactivation of the sperm gives them a greater power of resistance to freezing.

U.S. Pat. No. 4,429,542 to Sakao et al., U.S. Pat. No. 4,487,033 to Sakao et al., U.S. Pat. No. 3,893,308 to Barkay at al., and U.S. Pat. No. 4,480,682 to Kameta et al., all disclose different freezing methods which claim to improve the fertility of sperm samples. In all of these methods, the temperature of sperm in solution is lowered by various means which attempt to reduce the thermal shock and increase the survivability of the viable cells present. Most of these methods are, however, complex, cumbersome and expensive to utilize. Other freezing methods are also used including the method of rapidly freezing in liquid nitrogen vapors (Sherman J K, Improved Methods of Preservation of Humans Spermatozoa by Freezing and Freeze Drying, Fert. Steril. 14: 49–64, 1963), and the method of gradual freezing (Behrman et al., Heterologous and Homologous Insemination with Human Semen Frozen and Stored in a Liquid Nitrogen Refrigerator, Fert. Steril., 17: 457–466, 1966).

A disadvantage of the aforementioned methods resides in that low temperature preservation of the cells and tissues is accomplished by the ice crystallization process. As ice forms in the solution surrounding the cells or tissues, electrolytes and other solutes become progressively concentrated, quickly reaching concentrations which are damaging to the cells. This solute damage is attenuated by the addition of cryoprotectant chemicals such as glycerol, propylene glycol, ethylene glycol or dimethylsulfoxide. However, the cryoprotectants themselves can cause osmotic damage to the cell during their addition and removal. During cryoprotectant addition the cells and tissues undergo shrinkage and during removal they undergo swelling. The cryoprotectant removal process and associated cell swelling is particularly damaging. It is also the final step in the series of steps involved in the cryopreservation process and the one most often carried out in a clinical setting (e.g., operating room or emergency room). Therefore the process used for cryoprotectant removal must: (1) provide relatively rapid removal of the cryoprotectant, (2) provide a "closed" system to avoid potential contamination of the preparation, (3) be relatively simple to conduct and (4) require minimal specialized laboratory equipment. The present invention addresses each of these needs.

SUMMARY OF INVENTION

The present invention relates to a method of removing chemical compounds which protect cells (cryoprotectants) during low temperature preservation (cryopreservation). Typically such cryoprotectants are small molecular weight molecules such as glycerol, propylene glycol, ethylene glycol or dimethyl sulfoxide (DMSO). More particularly, this invention is directed to the use of specific enzymes to convert the cryoprotectant compounds into forms which cannot move across the cell membrane and enter the cell (are plasma membrane impermeable). Therefore, when applied to the cells, the enzymatic activity will shift the chemical potential of the cryoprotectants inside and outside the cells, causing the cryoprotectants to flow out of the cell, in turn become enzymatically modified, and thereby removed from the cells. The rate of conversion can be controlled.

This approach differs fundamentally from all previous methods in that it utilizes enzymes to effect cryoprotectant removal thereby minimize osmotic damage due to cell swelling and thus enhances the viability of cryopreserved cell populations.

DESCRIPTION OF THE PREFERRED EMBODIMENTS

Figure 1:
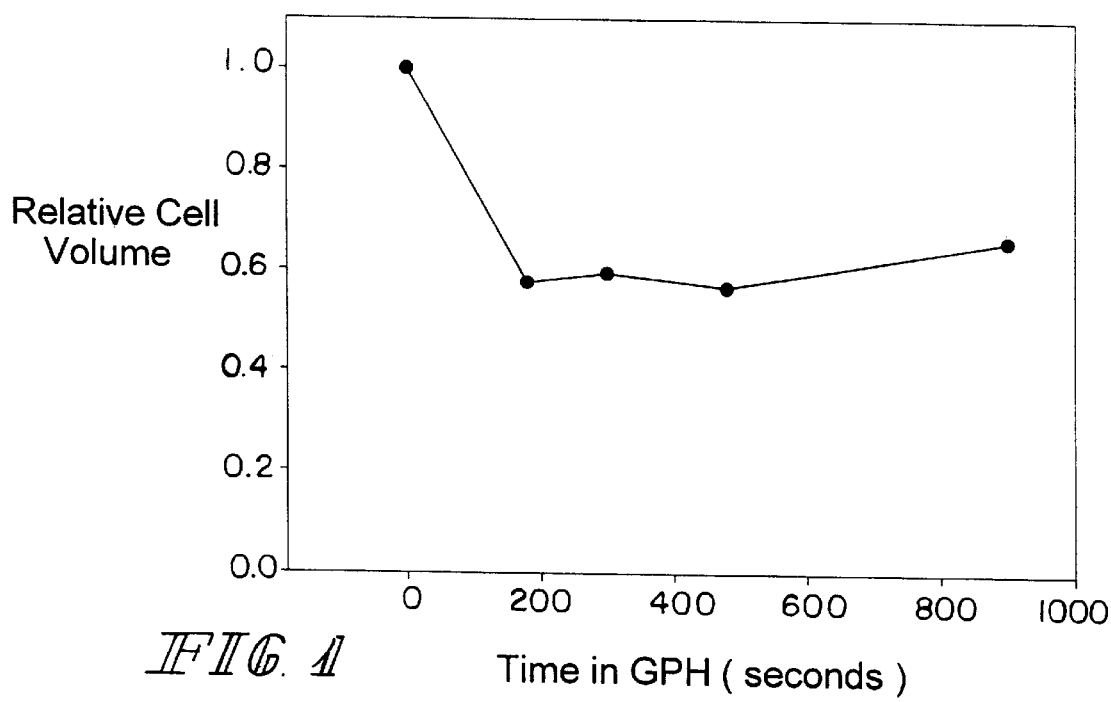
FIG. 1 is a graph showing relative human red blood cell (RBC) volume before (time 0) and during exposure to glycerol phosphate (GPH). These data show that human RBC volume is reduced and remains reduced over time. These data indicate that GPH is impermeable to the human RBC plasma membrane.

Specific language is used to describe several embodiments of this invention to promote an understanding of the invention and its principles. It must be understood that no specific limitation of the scope of this invention is intended by using this specific language. Any alteration and further modification of the described methods or devices, and any application of the principles of this invention are also intended that normally occur to one skilled in this art.

During standard equilibrium freezing methods to cryopreserve cells and tissues, as the cells are cooled to below their freezing point, ice begins to form. As ice forms in the solution surrounding the cells or tissues, electrolytes and other solutes become progressively concentrated, quickly reaching concentrations which are damaging to the cells. This solute damage is attenuated by the addition of cryoprotectant chemicals such as glycerol, propylene glycol, ethylene glycol or dimethylsulfoxide. However, the cryoprotectants themselves can cause osmotic damage to the cell during their addition and removal. During cryoprotectant addition the cells and tissues undergo shrinkage and during removal they undergo swelling. The cryoprotectant removal process and associated cell swelling is particularly damaging. It is also the final step in the series of steps involved in the cryopreservation process and the one most often carried out in a clinical setting (e.g., operating room or emergency room). Therefore the process used for cryoprotectant removal must: (1) provide a relatively rapid removal of the cryoprotectant, (2) provide a "closed" system to avoid potential contamination of the preparation, (3) be relatively simple to conduct and (4) require minimal specialized laboratory equipment.

Previous methods to avoid cell damage during the cryoprotectant removal process developed by Critser et al. (U.S. Pat. No. 5,700,632) utilized measurement of the osmotic tolerance limits of cells, predetermination of cell specific plasma membrane permeability coefficients, in combination with non-equilibrium thermodynamic mathematical modeling to predict optimal methods to step-wise remove cryoprotectants from cells. The fundamental basis for that approach is that as non-cryoprotectant solution is step-wise added to cells equilibrated with a given cryoprotectant concentration, the cells will, upon each solution addition step, undergo a given amount of cell swelling. Knowing the extent of this swelling and the maximal tolerated swelling, one can formulate the specific amount and rate of solution addition which will result in optimal cell survival at a maximal rate. However, this method requires expensive determination of each cell's membrane permeability coefficients, large volumes of non-cryoprotectant containing media to wash and remove the cryoprotectants from the cells and trades-off cell survival for maximal cryoprotectant removal rate. Removal rate is a critical factor in allowing cells and tissues to be practically utilized in many clinical settings (e.g., emergency blood transfusions).

The present invention addresses these shortcomings by utilizing a novel approach wherein cryoprotectant is removed from the cells and/or tissues by enzymatic conversion of the cryoprotectant chemical. A specific requirement of this method is that the final product of the reaction(s) is not permeable to the plasma membrane of the cell (so the product does not go into the cell). This method is effected by adding a specific enzyme or combination of enzymes and their cofactors (when required) to the cryopreserved cell suspension. Because the enzymes are relatively large, protein molecules they will act only upon extracelluar cryoprotectant. When the cryoprotectant is enzymatically converted to another chemical product, there is a shift in the chemical potential for the cryoprotectant (lowered on the outside of the cell). With the reduction of the cryoprotectant concentration on the outside of the cell, cryoprotectant from the inside will move out of the cell to maintain osmotic equilibrium (re-establish an equal chemical potential), lowering the cryoprotectant concentration inside the cell (i.e., removing the cryoprotectant from the cell). This is a continuous process with the rate being determined and controllable by the activity level of the enzyme specific for the cryoprotectant substrate, the concentration of the enzyme and the temperature at which the removal process is conducted. Therefore, when a faster rate is required, more enzyme can be added and/or the temperature of the reaction can be increased (within a physiological range). Unlike the earlier method of Critser et al., the cells do not swell during enzymatic removal/conversion of the cryoprotectant. The accumulation of cell membrane impermeable solute maintains the cell's volume below its isosmotic volume.

Enzyme Kinetics

The invention utilizes principles developed in the area of the biochemistry of enzyme kinetics. Those fundamental principles are briefly described. Enzymes have enormous catalytic power. They accelerate reactions by factors of at least a million. Enzymes are highly specific both in terms of the reaction they catalyze and in terms of the substrates they act upon. An enzyme usually catalyzes a single chemical reaction or a set of closely related reactions. The form of the equations used to describe enzymatically-catalyzed reactions is classically:

$$E + S \rightarrow ES \rightarrow E + P,$$

where E is the enzyme, S is the substrate, ES is the enzyme-substrate complex and P is the product. The form of the equations to describe enzymatically-catalyzed reactions used in the following description of the invention is:

$$\text{Substrate} + \text{cofactor(s)} \xrightarrow{\text{enzyme}} \text{product} + \text{cofactor(s)},$$

where cofactors are compounds such as ATP (a phosphate source) or NAPDH (a hydrogen donor source).

EXAMPLES

Example 1
Use of Glycerol Kinase to Remove Glycerol from Cells in a Single Step Process Glycerol kinase (GK) catalyzes the following reaction:

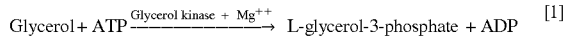

$$\text{Glycerol} + \text{ATP} \xrightarrow{\text{Glycerol kinase} + \text{Mg}^{++}} \text{L-glycerol-3-phosphate} + \text{ADP} \quad [1]$$

Glycerol kinase is found widely in nature (Thorner and Paulus, 1973). In microorganisms GK is involved in the utilization of glycerol as a carbon source. In mammals, the enzyme in involved in fat and sugar metabolism (Kida et al., 1973). GK phosphorylates glycerol exclusively to L-[[alpha]]-glycerophosphate. The reaction is essentially irreversible and $Mg^{2+}$ is required (Zwaig and Lin, 1966, Hayashi and Lin, 1967; Thorner and Paulus, 1973). The activity of this enzyme is characterized in terms of the ability of the enzyme to convert 1.0 μM glycerol to L-glycerol, 3-phosphate/min at 25° C.

Many cells, such as red blood cell, used widely in transfusion medicine, are cryopreserved using 1–3 M concentrations of glycerol. One of the major rate limiting factors using current protocols for freezing red blood cells, is the time it takes to remove the glycerol from the cells before they can safely be transfused into a patient. This is because, using standard washing approaches for glycerol removal, the red cells will undergo extreme swelling and lyse unless the washing procedure is performed very slowly. Currently it takes approximately 1 hour to deglycerolize one unit of blood, which is far too long a time for emergency situations. Red blood cells, like other mammalian cells, can be treated prior to preservation by removing them from their normal endogenous milieu. In the specific case of red blood cell, they can be washed free of plasma and re-suspended into an artificial medium. This step will prevent the interaction of the enzymes used in these procedures with substrates in those biological fluids.

Based upon the biochemical characteristics of glycerol kinase, it is possible to calculate the rate conversion of glycerol to its phosphorylated, non-membrane permeable form as follows:

A standard blood bag (500 ml) containing packed red cells equilibrated with a 1 molar glycerol concentration will contain 500,000 μmoles of glycerol. Using a standard glycerol kinase preparation with an enzymatic activity of 100 units per milligram (mg) of protein and adding 500 mg of enzyme to the blood bag (1 mg protein/ml) will have a total of 50,000 enzymatic units. Dividing 500,000 (μmoles of glycerol) by 50,000 (enzyme units) results in the clearance of glycerol from the red cells in 10 minutes. Because the enzymatic activity of GK is increased with increasing temperature, conducting this process at, for example, 37° C. would decrease the total time for glycerol removal by approximately 50–100%.

Experimental Validation of Method

Rationale: A fundamental premise of this procedure is that the glycerol, used as a cryoprotectant solute, will be rendered impermeable to the plasma membrane of cells when phosphorylated by glycerol kinase to Lα-glycerophosphate (LαGPH) and that LαGPH is non-toxic (non-lytic). Finally, this procedure must effectively remove glycerol from cells without lysis. Therefore, experimental proof of principle was developed. Three experiments were conducted: (1) Determination of human red cell volume in the presence of LαGPH; (2) Determination of human red cell lysis in the presence of LαGPH and (3) Determination of human red blood cell integrity following glycerol removal using glycerol kinase. The first experiment was conducted to determine whether LαGPH is permeable to the plasma membrane. The second experiment was conducted to determine whether the LαGPH is toxic (lytic) to human red cells. The third experiment was conducted to demonstrate the effectivness of glycerol removal from human red blood cells using an enzymatic method.

Example 1a
Determination of Human RBC Cell Volume in the Presence of Glycerol Phosphate Media: 950 mg of LαGPH were placed into 6.42 ml of isotonic phosphate buffered saline (PBS) to yield a 0.4 M concentration of LαGPH. The corresponding osmolality was 1340±3 mOsm.

Experimental procedure: Human red cells were abruptly exposed to the 0.4 M LαGPH solution and the cell volume over time was determined using a modified Coulter counter apparatus. The results are shown in FIG. 1. Human RBC volume was reduced to 58% of their isosmotic volume within 3 minutes and the cell volume remained reduced for 15 minutes. These data demonstrate that LαGPH is impermeable to the human red cell plasma membrane.

Example 1b
Determination of Human RBC Lysis in the Presence of LαGPH

Media: Reagent grade distilled water (negative control; 100% lysis expected), isotonic PBS (positive control, 0% lysis expected) and 1180 and 1340 mOsm glycerolphosphate solutions were used.

Figure 2:
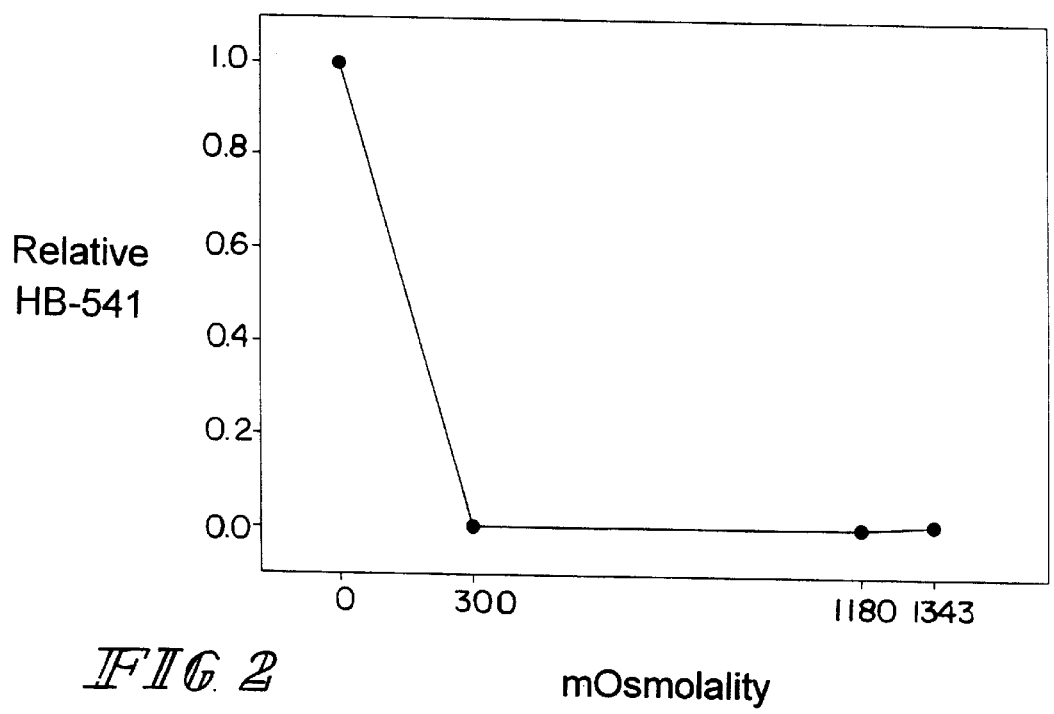
FIG. 2 is a graph showing relative hemoglobin in suspension, as measured by spectrophotometric absorbance at 541 nm, in samples exposed to various osmolalities. Negative control (0 mOsm) showed 100% lysis. Positive control (300 mOsm) showed 0% lysis. Samples exposed to hyperosmotic glycerol phosphate solutions showed lysis values not different from the positive control.

Experimental procedure: Human red cells were exposed for 20 minutes to one of the four treatment media listed above. After 20 minutes, the cells were placed into a spectrophotometer and absorbance at 541 nm measured to determined the amount of hemoglobin in free solution as a measure of cell lysis. The distilled water treatment was used as the negative control and assumed to produce 100% cell lysis. The other values were normalized to this value. The results are shown in FIG. 2. No cell lysis was observed in either the isosmotic PBS control (positive control) or the LαGPH solutions. These data indicated that concentrations of LαGPH to remove glycerol from human red cells are not damaging.

Example 1c
Demonstration of Effective Removal of Glycerol from Human RBC Using an Enzymatic Method Media: Reagent grade distilled water (negative control; 100% lysis expected), isotonic PBS (positive control, 0% lysis expected) 1.0M glycerol in isotonic PBS, 1.0M ATP and 100 units of glycerol kinase were used.

Experimental procedure: Human red cells were equilibrated with 1.0M glycerol (using a standard blood banking procedure) then divided into two groups. Group one was equilibrated with glycerol only and group two was equilibrated with glycerol then exposed to the glycerol kinase and ATP for 5 minutes. Both groups were then abruptly diluted 10 times with isotonic PBS, centrifuged and absorbance measured at 541 nm to determined the amount of hemoglobin in free solution as a measure of cell lysis. The distilled water treatment was used as the negative control and assumed to produce 100% cell lysis. The other values were normalized to this value. As expected, cells exposed to isotonic PBS only and cells equilibrated with 1M glycerol then subjected to deglycerolization using the enzymatic method resulted in 0% absorbance (no cell lysis). However, cells which had been equilibrated with 1M glycerol and then abruptly diluted with isotonic PBS exhibited 77% lysis normalized to the negative control. These data demonstrate that the glycerol kinase method results in effective deglycerolization of human red blood cells without cell lysis.

Example 2
Use of Propanediol Dehydratase and Acetate Kinase to Remove 1,2-Propanediol or Ethylene Glycol from Cells Propanediol dehydratase (E.C. # 4.2.1.28) catalyzes the following reactions:

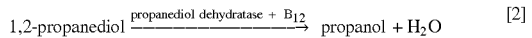

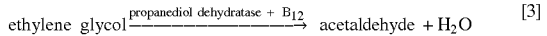

Propanediol dehydratase is a naturally occurring enzyme involved with glycerolipid metabolism. Once the cryoprotectant substrates are converted to propanol and acetaldehyde, respectively, the product aldehydes can be removed from the cell suspension by an imine-forming reaction with, e.g., a primary amine immobilized on a solid, optionally magnetic, support, e.g., aminopropyl silica. Optionally the enzyme reaction can be carried out in the presence of the immobilized amines. The treated solid support is then separated from the cell suspension.

Example 3
Use of Methyl Sulfoxide Reductase and Thioether S-Methyltransferase to Remove Dimethyl Sulfoxide from Cells Methyl sulfoxide reductase (E.C. # 1.8.4.5) catalyzes the following reaction:

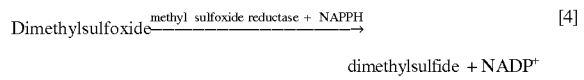

At this point, the dimethylsulfide can be adsorbed onto beads with immobilized $Sn^{+2}$.

Alternatively, a second enzymatic reaction can be utilized in which thioether S-methyltransferase (E.C. # 2.1.1.96) catalyzes the following reaction:

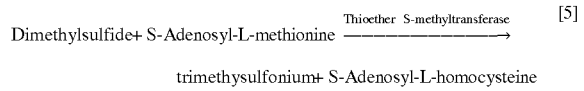

Subsequent adsorption of the trimethylsulfonium ion out of solution and isolation of the cell population, e.g., by centrifugation, with optional washing with, e.g., isotonic saline, provides a population of cells for medical or research use.

Further Aspects of this Invention

In some cases it may be necessary or desirable to remove the enzymes and/or the chemical products of the enzymatic reactions from the solution containing the cells or tissues. A further aspect of this invention is the use of specific components for this type of removal of the enzymes and the chemical products of the enzymatic reactions. In the case of enzyme removal, the following specific design aspects are included:

Solid Phase Enzymes: The enzyme or enzymes required for the particular chemical reaction(s) used to remove cryoprotectants for cells may be either chemically bound to the inner wall of the storage vessel (e.g., the inner wall of a plastic blood bag) using for example direct chemical bonding, where the enzyme protein is chemically bonded to a solid support, e.g., a microparticulate composition or a container, or immuno-bonded, where an antibody is made to the protein enzyme, the antibody is chemically bonded to the vessel wall and the enzyme then bound to the antibody. In this type of system the enzymes will be sequestered to the solid support and never enter into solution. This approach allows retention of the enzymes when the cells are removed for use. Depending upon the surface area of the cell or tissue vessel, more area may be required to bind all of the enzyme(s). In this case antibodies to the enzyme can be bond to the tubing connected to the vessel and the enzyme bond as the cells or tissues are transfused or decanted.

Another solid phase enzyme configuration involves the bonding of the enzyme to metallic (magnetic) particles. When the reaction is complete a magnet is applied to the bottom of the vessel containing the cell or tissues so that the beads are drawn to the magnet. The cell or tissue suspension can then be poured off retaining the metallic particles in the vicinity of the magnet.

Removal of the chemical products: Many of the final products of the reaction described in this invention result ultimately in a chemically charged molecule (e.g., phosphorylated molecules carry a negative charge and the sulfonium molecule a positive charge). A additional aspect of this invention is the use of specific sorbent compositions which can be incorporated into optionally magnetic particles or into tubing or plasticware through which or into which the cell an/or tissue samples with the final chemical products will be placed. Contact of the solution surrounding the cells or tissues with these adsorbent or absorbent (sorbent) materials effect removal of the products via a predetermined substantially selective interaction between the product and the composition. For example, passing a cell or tissue sample for which dimethylsulfoxide was used as the cryoprotectant will end with trimethylsulfonium as a final product. Since the sulfonium has a positive charge, if it were passed through or over a an anionic resin/polymer or other negative charged surface, the trithylsulfonium molecules bind to the polymer and are thereby removed from the solution. Likewise using positively charged polymeric materials can be used to remove negatively charged molecules (e.g., glycerol 3-phosphate, propionyl phosphate or acetyl phosphate). Using this approach it is possible to remove the chemical products of the reactions before the cell or tissues are used for transfusion, transplantation, insemination or other applications.

While the invention has been described in detail, the same is to be considered as illustrative and not restrictive in character, it being understood that only the preferred embodiment has been described and that all changes and modifications that come within the spirit of the invention are desired to be protected.

We claim:
1. A method for removing cryoprotectant from animal cells which have been cryopreserved in a solution containing a cryoprotectant which is permeable to the cells, said method comprising the steps of
    contacting the cryoprotectant solution containing the cells with an enzyme which enzymatically converts the cryoprotectant to a product not permeable to the cells; and
    maintaining cell viability during the enzymatic conversion.

2. The method of claim 1 wherein the rate of enzymatic conversion is controlled to minimize osmotic damage to the cryopreserved cells by enzyme selection, by adjusting temperature, by adjusting enzyme concentration, or by adjusting a combination of such parameters.

3. The method of claim 2 further comprising the step of removing the enzyme conversion product from the cells.

4. The method of claim 1 wherein the enzyme used in the enzymatic conversion is bound to a solid support.

5. The method of claim 4 wherein the solid support comprises a magnetic component.

6. The method of claim 1 further comprising the step of removing the enzyme conversion product from the cells.

7. The method of claim 6 wherein the enzymatic conversion product is removed by contacting same with a sorbent material for adsorption or adsorption of the product.

8. The method of claim 7 wherein the sorbent material comprises a magnetic component.

9. The method of claim 7 where the sorbent material comprises $Sn^{+2}$.

10. The method of claim 6 wherein the enzyme conversion product is an aldehyde and the sorbent material comprises imine-forming amines covalently bound to a solid support.

11. The method of claim 1 wherein the said cryoprotectant is glycerol, 1,2-propanediol, ethylene glycol or dimethysulfoxide.

12. The method of claim 1 wherein the animal cells are sperm cells.

13. The method of claim 1 wherein the animal cells are red blood cells.

14. The method of claim 1 wherein the animal cells are platelets.

15. The method of claim 1 wherein the animal cells are hematopoietic stem cells.

16. The method of claim 1 wherein the animal cells are granulocytes.

17. The method of claim 1 wherein the animal cells are pancreatic islets or islet cells.

18. The method of claim 1 wherein the animal cells are oocytes.

19. The method of claim 1 wherein the animal cells are embryos.

* * * * *